United States Patent
Kulkarni et al.

(10) Patent No.: US 6,184,412 B1
(45) Date of Patent: Feb. 6, 2001

(54) PROCESS FOR MANUFACTURE OF N-ALKOXY(OR ARYLOXY)CARBONYL ISOTHIOCYANATE DERIVATIVES IN THE PRESENCE OF N,N-DIALKYLARYLAMINE CATALYST AND AQUEOUS SOLVENT

(75) Inventors: Shekhar V. Kulkarni; Vijay C. Desai, both of Shawnee, KS (US)

(73) Assignee: Bayer Corporation, Pittsburgh, PA (US)

( * ) Notice: Under 35 U.S.C. 154(b), the term of this patent shall be extended for 0 days.

(21) Appl. No.: 09/329,405

(22) Filed: Jun. 10, 1999

(51) Int. Cl.[7] ................................................. C07C 261/00
(52) U.S. Cl. ........................ 560/137; 560/148; 558/19
(58) Field of Search ................................. 560/137, 148; 558/19

(56) References Cited

U.S. PATENT DOCUMENTS

| | | | | |
|---|---|---|---|---|
| 2,331,276 | * | 10/1943 | Pitman | 554/42 |
| 2,462,433 | * | 2/1949 | Searle | 558/10 |
| 4,482,500 | * | 11/1984 | Lewellyn | 558/234 |
| 4,659,853 | * | 4/1987 | Fu et al. | 558/19 |
| 4,778,921 | * | 10/1988 | Lewellyn et al. | 560/137 |
| 5,194,673 | * | 3/1993 | Wang et al. | 560/137 |

OTHER PUBLICATIONS

Chem. Ber. 116, (month unavailable) 1983, Joachim Goerdeler et al, Zur Kenntnis von Isothiocyanaten der Thiokohlensäure–O–ester.

* cited by examiner

*Primary Examiner*—Gary Geist
*Assistant Examiner*—Taylor V Oh
(74) *Attorney, Agent, or Firm*—Joseph C. Gil; Carol Marmo

(57) ABSTRACT

The present invention provides a process for making N-alkoxy(or aryloxy)carbonyl isothiocyanate derivatives by reacting a chloroformate with a thiocyanate, in the presence of an aqueous solvent and a catalytic amount of a N,N-dialkylarylamine, to produce a N-alkoxy(or aryloxy) carbonyl isothiocyanate intermediate product, wherein the intermediate product is converted to a N-alkoxy(or aryloxy) carbonyl isothiocyanate derivative in high yield and purity.

19 Claims, No Drawings

PROCESS FOR MANUFACTURE OF N-ALKOXY(OR ARYLOXY)CARBONYL ISOTHIOCYANATE DERIVATIVES IN THE PRESENCE OF N,N-DIALKYLARYLAMINE CATALYST AND AQUEOUS SOLVENT

TECHNICAL FIELD OF THE INVENTION

The field of the present invention is the manufacture of carbonyl isothiocyanate derivatives. More particularly, the present invention pertains to an improved process for preparing N-alkoxy(or aryloxy)carbonyl isothiocyanate derivatives, wherein the improvement comprises the presence of a N,N-dialkylarylamine as a catalyst in the reaction process, and the presence of an aqueous solvent in the reaction process.

BACKGROUND OF THE INVENTION

Derivatives of carbonyl isothiocyanates are well known in the art, and various methods for their production are also known in the art.

U.S. Pat. No. 4,659,853 discloses a process for producing derivatives of alkoxy, aryloxy and alkene isothiocyanates by reacting a haloformate, an alkali, alkaline earth metal, lead or ammonium thiocyanate and a compound having the formula $R^1$—Y—H wherein $R^1$ is an alkyl, aryl or alkoxy, Y is oxygen, sulfur or N—$R^2$, and $R^2$ is hydrogen or $R^1$; in the presence of a solvent or water and a catalyst. Suitable catalysts include pyridine, quinoline, pyrimidine, pyrazine, quinoxaline and the like.

U.S. Pat. No. 4,778,921 describes a process for the preparation of alkoxy and aryloxy isothiocyanates which includes the reaction of a haloformate and an alkali or alkaline earth metal thiocyanate in the presence of water and a catalyst. The catalyst comprises a six-membered mononuclear or ten-membered fused polynuclear aromatic, heterocyclic compound having one or two nitrogen atoms as the only hetero atoms in the ring.

U.S. Pat. No. 5,194,673 discloses a process for producing alkoxy and aryloxy isothiocyanates by the reaction of a haloformate and an alkali or alkaline earth metal thiocyanate in the presence of water and a catalyst. A co-catalyst is also used in the process to accelerate the reaction rate, increase product purity, and reduce the adverse effects of impurities in the thiocyanate reactants.

In the publication, Chem. Ber. 116, 2044, (1983), it is reported that the use of an aromatic heterocyclic nitrogen catalyst such as pyridine in carbon tetrachloride produced an alkoxythiocarbonyl isothiocyanate wherein the yield was only about 52%.

The most prevalent prior art methods comprise (i) the formation of the carbonyl isothiocyanate, (ii) the recovery and purification thereof, and (iii) the final reaction thereof with the appropriate co-reactant to produce the desired derivative. However, the known methods result in carbonyl isothiocyanate of low yield and purity. Thus, there is a need in the art for a process to produce carbonyl isothiocyanate derivatives in high yield and purity.

BRIEF SUMMARY OF INVENTION

The present invention provides a process for the preparation of N-alkoxy(or aryloxy)carbonyl isothiocyanate derivatives which includes reacting a chloroformate compound of the general formula (I)

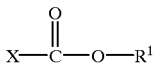
(I)

wherein $R^1$ represents a $C_1$–$C_8$ alkyl radical, a $C_2$–$C_4$ alkenyl radical, or a $C_6$–$C_{10}$ aryl radical; and X represents a halogen atom; with a thiocyanate of the general formula (II)

(II)

wherein M represents an alkali or alkaline earth metal, lead, or $NH_4$, in the presence of an aqueous solvent, and in the presence of a catalytic amount of a N,N-dialkylarylamine of the general formula (III)

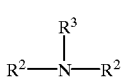
(III)

wherein $R^2$ each represents a $C_1$–$C_8$ alkyl radical or a $C_3$–$C_6$ alkenyl radical, or $R^2$ together represents a $C_5$ saturated heterocyclic ring or a $C_4$ saturated heterocylic ring wherein O may be part of the ring; and $R^3$ represents an aryl group that can be a phenyl, a naphthyl, a substituted phenyl or a substituted naphthyl; to produce a N-alkoxy(or aryloxy) carbonyl isothiocyanate intermediate product of the general formula (IV)

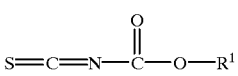
(IV)

wherein $R^1$ is as defined above in formula (I); and reacting a compound of the general formula (V)

(V)

wherein $R^4$ represents a $C_1$–$C_{10}$ alkyl radical, a $C_6$–$C_{10}$ aryl radical or a $C_1$–$C_8$ alkoxy radical, and Y represents oxygen, sulfur or $NR^5$, wherein $R^5$ represents hydrogen or $R^4$, with the intermediate product (IV) to produce a N-alkoxy(or aryloxy)carbonyl isothiocyanate derivative of the general formula (VI)

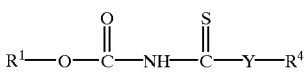
(VI)

wherein $R^1$ is as defined above in formula (I), and $R^4$ and Y are as defined above in formula (V).

DETAILED DESCRIPTION OF THE INVENTION

The present invention provides a process for producing carbonyl isothiocyanate derivatives. In particular, the present process is used to produce N-alkoxy(or aryloxy) carbonyl isothiocyanate derivatives in high yield and purity. The process comprises reacting a chloroformate compound of the general formula (I)

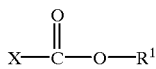
(I)

wherein R$^1$ represents a C$_1$–C$_8$ alkyl radical, a C$_2$–C$_4$ alkenyl radical or a C$_6$–C$_{10}$ aryl radical; and X represents a halogen atom, with a thiocyanate of the general formula (II)

MSCN  (II)

wherein M represents an alkali or alkaline earth metal, lead, or NH$_4$, in the presence of an aqueous solvent, and in the presence of a catalytic amount of a N,N-dialkylarylamine of the general formula (III)

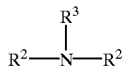
(III)

wherein R$^2$ each represents a C$_1$–C$_8$ alkyl radical or a C$_3$–C$_6$ alkenyl radical, or R$^2$ together represent a C$_5$ saturated heterocyclic ring or a C$_4$ saturated heterocyclic ring wherein O may be part of the ring; and R$^3$ represents an aryl group that can be a phenyl, a naphthyl, a substituted phenyl or a substituted naphthyl; to produce a N-alkoxy(or aryloxy) carbonyl isothiocyanate intermediate product of the general formula (IV)

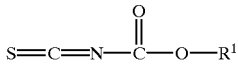
(IV)

wherein R$^1$ is as defined above in formula (I); and reacting a compound of the general formula (V)

R$^4$—Y—H  (V)

wherein R$^4$ represents a C$_1$–C$_{10}$ alkyl radical, a C$_6$–C$_{10}$ aryl radical or a C$_1$–C$_8$ alkoxy radical, and Y represents oxygen, sulfur or NR$^5$, wherein R$^5$ represents hydrogen or R$^4$, with the intermediate product (IV) to produce a N-alkoxy(or aryloxy)carbonyl isothiocyanate derivative of the general formula (VI)

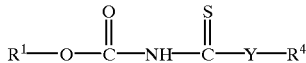
(VI)

wherein R$^1$ is as defined above in formula (I), and R$^4$ and Y are as defined above in formula (V).

The process of the present invention may be conducted in a one-pot process.

The process according to the invention is generally carried out at atmospheric pressure. The reaction of the chloroformate (formula I) with the thiocyanate (formula II) is carried out at a temperature of from about –10° C. to about 40° C.; and preferably at a temperature of from about 0° C. to about 10° C. The chloroformate is added to the reaction mixture at a rate such that the temperature of the reaction remains in the desired range. The reaction time for this step in the process of the invention is up to about 16 hours; and preferably the reaction time is from about 1 hour to about 4 hours. The progress of the reaction is monitored by liquid chromatography analysis of the reaction mixture to determine the amount of unreacted thiocyanate.

Suitable chloroformates for use in the process of the present invention include methyl, ethyl, propyl, isopropyl, butyl, isobutyl, amyl, hexyl, 2-ethylhexyl, benzyl, phenyl, and allyl chloroformates. In a preferred embodiment, the chloroformate is either methyl chloroformate or propyl chloroformate.

Suitable thiocyanates for use in the process of the present invention include metal, lead and ammonium thiocyanates. Suitable thiocyanates include sodium, lithium, potassium, rubidium, cesium, beryllium, magnesium, calcium, strontium, and barium thiocyanates. In a preferred embodiment, the thiocyanate is sodium thiocyanate.

The reaction of the chloroformate and thiocyanate is carried out in the presence of a catalytic amount of a N,N-dialkylarylamine (formula III), and in the presence of an aqueous solvent.

Suitable N,N-dialkylarylamines for use as a catalyst in the reaction of the present invention include N,N-dimethylaniline, N,N-dimethyl-1-naphthylamine, N,N-dimethyl-p-toluidine, N,N-diethylaniline, N,N-diallylaniline, 1-phenylpiperidine and 4-phenylmorpholine. In a preferred embodiment, the N,N-dialkylarylamine catalyst is N,N-dimethylaniline. The amount of catalyst present in the reaction mixture is such that it comprises from about 0.1% to about 30% by mole based on the chloroformate; and preferably from about 3% to about 9% by mole.

Suitable solvents for use in the process of the present invention include aqueous solvents such as water.

In an embodiment of the present invention, following completion of the reaction between the chloroformate and the thiocyanate, an acid such as aqueous hydrochloric acid or aqueous sulfuric acid may be added to the reaction mixture to neutralize the catalyst.

The reaction of the N-alkoxy(or aryloxy)carbonyl isothiocyanate intermediate product of formula IV with the compound of formula V is carried out at a temperature of from about –10° C. to about 100° C., and preferably from about 25° C. to about 50° C.; for a time period of up to about 16 hours, and preferably from about 2 hours to about 4 hours.

Suitable compounds represented by formula V for use in the process of the present invention include alcohols such as methanol, ethanol, n-propyl alcohol, isopropyl alcohol, n-butyl alcohol, isobutyl alcohol, sec-butyl alcohol, amyl alcohols, hexyl alcohols, heptyl alcohols, cyclopentyl alcohol, cyclohexyl alcohol, allyl alcohols, benzyl alcohol; amines such as methylamine, ethylamine, hexylamine, isopropylamine, isobutylamine, amylamines, cyclohexylamine, octylamine, benzylamine, dimethylamine, diethylamine, dipropylamine, dibutylamine, diphenylamine, dibenzylamine, ethylmethylamine, N-methylaniline; mercaptans such as methyl mercaptan, ethyl mercaptan, propyl mercaptan, butyl mercaptan, amyl mercaptans, hexyl mercaptans, benzyl mercaptans, allyl mercaptans and the like. Preferred compounds of formula V are methanol and propanol.

The invention is further illustrated but is not intended to be limited by the following examples in which all parts and percentages are by weight unless otherwise specified.

EXAMPLES

Example 1

Preparation of MTC, With Neutralization of the Catalyst 7.2 grams (0.06 mole) of 99% pure N,N-dimethylaniline was added to a solution of 86.0 grams (1.04 moles) of 98% pure NaSCN, in 170.5 grams of water, and the mixture was cooled to a temperature of from about 0° C. to about 5° C. with stirring. About 95.5 grams (1.00 mole) of 99% pure methyl chloroformate was added to the stirred reaction mixture over a period of about 2 hours, maintaining the temperature of the reaction mixture from about 0° C. to about 5° C. Following this addition step, the reaction mixture was stirred for about 1 hour. The reaction mixture was then chilled to a temperature of about 0° C. A chilled (about 0° C.) solution of 6.18 grams (0.06 mole) of sulfuric acid was dissolved in 174 ml of water, and this solution was added to the reaction mixture (to neutralize the catalyst) over a time period of about 10 minutes. The mixture was then stirred at a temperature of about 0° C. for about 15 minutes. The stirring was then stopped and the mixture was allowed to settle for about 15 minutes at a temperature of about 0° C. The mixture separated into an aqueous phase and an organic phase. The desired N-methoxycarbonyl isothiocyanate product ("MITC") was contained within the organic phase.

While maintaining the reaction mixture at a temperature of about 0° C., the lower organic layer (which included the intermediate MITC product) was slowly added to about 277.6 grams (8.68 moles) of methanol, over a time period of about 1 hour, while the temperature of the reaction mixture was maintained between about 30° C. and about 40° C. The reaction mixture was then stirred at a temperature of from about 30° C. to about 40° C. for about 2 hours. The solvent-free purity of N-methoxycarbonyl-O-methylthionocarbamate ("MTC") in the reaction mixture at this point was 98.5% (no trace of the isomer MeOOC-SCN was observed using a liquid chromatograph).

Analysis by liquid chromatography of the resulting solution of MTC in methanol resulted in a yield of 93.4% based on methyl chloroformate.

Example 2
Preparation of MTC; Without Neutralizing the Catalyst 22.0 grams (0.18 mole) of 99% pure N,N-dimethylaniline was added to a solution of 248.3 grams (3.00 moles) of 98% pure NaSCN, in 595.0 grams of water. The mixture was cooled to a temperature of between about 0° C. and about 5° C. with stirring. About 274.9 grams (2.88 moles) of 99% pure methyl chloroformate was added to the stirred reaction mixture over a time period of about 2 hours, maintaining the temperature of the reaction mixture between about 0° C. and about 5° C. Following addition of the methyl chloroformate, the reaction mixture was then stirred at a temperature of between about 0° C. and about 5° C. for a period of about 1 hour. The stirring was then stopped and the phases were allowed to separate into an organic and an aqueous phase at a temperature of about 0° C., without prior neutralization of the catalyst. The organic layer (containing the intermediate "MITC" product) was slowly added to 800.0 grams (25.0 moles) of methanol over a period of about 1 hour, while the temperature of the reaction mixture was maintained between about 30° C. and about 40° C. The reaction mixture was then stirred at a temperature of from about 30° C. to about 40° C. for about 2 hours.

Analysis by liquid chromatography of the resulting solution of N-methoxycarbonyl-O-methylthionocarbamate ("MTC") in methanol indicated a yield of 93% based on methyl chloroformate.

Example 3
Preparation of PTC; Without Neutralizing the Catalyst 22.0 grams (0.18 mole) of 99% pure N,N-dimethylaniline was added to a solution of 260.4 grams (3.15 moles) of 98% pure NaSCN, in 640.0 grams of water. The mixture was cooled to a temperature of between about 0° C. and about 5° C. with stirring. 376.8 grams (3.01 moles) of 98% pure propyl chloroformate was added to the stirred reaction mixture over a period of about 2 hours, maintaining the temperature of the reaction mixture between about 0° C. and about 5° C. Following addition of the propyl chloroformate, the reaction mixture was stirred at a temperature of between about 0° C. and about 5° C. for a period of about 4 hours. The stirring was then stopped and the phases were allowed to separate into an organic phase and an aqueous phase at a temperature of about 0° C., without prior neutralization of the catalyst. The desired N-propoxycarbonyl isothiocyanate product ("PITC") was contained within the organic phase. The organic layer (containing the intermediate PITC product) was slowly added to 540.0 grams (9.0 moles) of propanol over a period of about 1 hour. During this addition step, the temperature of the organic layer was maintained at about 0° C.; while the temperature of the resultant reaction mixture was maintained between about 30° C. and about 40° C. The reaction mixture was then stirred at a temperature of from about 30° C. to about 40° C. for about 2 hours.

Analysis by liquid chromatography of the resulting solution of N-propoxycarbonyl-O-propylthionocarbamate ("PTC") in propanol indicated a yield of 98% based on propyl chloroformate.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of N-alkoxy(or aryloxy) carbonyl isothiocyanate derivatives comprising:

a) reacting a chloroformate compound of the general formula (I)

(I)

wherein $R^1$ represents a $C_1$–$C_8$ alkyl radical, a $C_2$–$C_4$ alkenyl radical, or a $C_6$–$C_{10}$ aryl radical, and X represents a halogen atom, with a thiocyanate of the general formula (II)

MSCN (II)

wherein M represents an alkali or alkaline earth metal, lead, or $NH_4$, in the presence of an aqueous solvent, and in the presence of a catalytic amount of a N,N-dialkylarylamine of the general formula (II)

(III)

wherein $R^2$ each represents a $C_1$–$C_8$ alkyl radical or a $C_3$–$C_6$ alkenyl radical, or $R^2$ together represent a $C_5$ saturated heterocyclic ring or a $C_4$ saturated heterocyclic ring wherein O may be part of the ring; and $R^3$ represents an aryl group that can be a phenyl, a naphthyl, a substituted phenyl or a substituted naphthyl, to produce a N-alkoxy(or aryloxy)carbonyl isothiocyanate intermediate product of the general formula (IV)

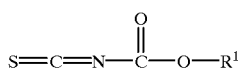
(IV)

wherein $R^1$ is as defined above in formula (I); and b) reacting the intermediate product (IV) with a compound of the general formula (V)

wherein $R^4$ represents a $C_1$–$C_{10}$ alkyl radical, a $C_6$–$C_{10}$ aryl radical or a $C_1$–$C_8$ alkoxy radical, and Y represents oxygen, sulfur, or $NR^5$, wherein $R^5$ represents hydrogen or $R^4$, to produce a N-alkoxy(or aryloxy)carbonyl isothiocyanate derivative of the general formula (VI)

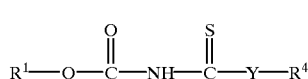
(VI)

wherein $R^1$ is as defined above in formula (I), and $R^4$ and Y are as defined above in formula (V).

2. The process of claim 1 wherein the chloroformate compound is selected from the group consisting of methyl, ethyl, propyl, isopropyl, butyl, isobutyl, amyl, hexyl, 2-ethylhexyl, benzyl, phenyl, and allyl chloroformates.

3. The process of claim 1 wherein the chloroformate compound is selected from the group consisting of methyl chloroformate and propyl chloroformate.

4. The process of claim 1 wherein the thiocyanate is selected from the group consisting of sodium, lithium, potassium, rubidium, cesium, beryllium, magnesium, calcium, strontium, and barium thiocyanates.

5. The process of claim 1 wherein the thiocyanate is sodium thiocyanate.

6. The process of claim 1 in step a) wherein the reaction is carried out at a temperature of from about −10° C. to about 40° C.

7. The process of claim 1 in step a) wherein the reaction is carried out at a temperature of from about 0° C. to about 10° C.

8. The process of claim 1 in step b) wherein the reaction is carried out at a temperature of from about −10° C. to about 100° C.

9. The process of claim 1 in step b) wherein the reaction is carried out at a temperature of from about 25° C. to about 50° C.

10. The process of claim 1 wherein the N,N-dialkylarylamine is selected from the group consisting of N,N-dimethylaniline, N,N-dimethyl-1-naphthylamine, N,N-dimethyl-p-toluidine, N,N-diethylaniline, N,N-diallylaniline, 1-phenylpiperidine, and 4-phenylmorpholine.

11. The process of claim 1 wherein the N,N-dialkylarylamine is N,N-dimethylaniline.

12. The process of claim 1 wherein the N,N-dialkylarylamine comprises from about 0.1% to about 30% by mole based on the chloroformate.

13. The process of claim 1 wherein the N,N-dialkylarylamine comprises from about 3% to about 9% by mole based on the chloroformate.

14. The process of claim 1 wherein the compound of formula V is selected from the group consisting of alcohols, amines and mercaptans.

15. The process of claim 1 wherein the compound represented by formula V is selected from the group consisting of methanol, ethanol, n-propyl alcohol, isopropyl alcohol, n-butyl alcohol, isobutyl alcohol, sec-butyl alcohol, amyl alcohols, hexyl alcohols, heptyl alcohols, cyclopentyl alcohol, cyclohexyl alcohol, allyl alcohols, benzyl alcohol, methylamine, ethylamine, hexylamine, isopropylamine, isobutylamine, amylamines, cyclohexylamine, octylamine, benzylamine, dimethylamine, diethylamine, dipropylamine, dibutylamine, diphenylamine, dibenzylamine, ethylmethylamine, N-methylaniline, methyl mercaptan, ethyl mercaptan, propyl mercaptan, butyl mercaptan, amyl mercaptans, hexyl mercaptans, benzyl mercaptans, and allyl mercaptans.

16. The process of claim 1 wherein the compound represented by formula V is selected from the group consisting of methanol and propanol.

17. The process of claim 1 wherein the aqueous solvent is water.

18. The process of claim 1 in step a) further comprising the addition of an acid to the reaction mixture to neutralize the catalyst.

19. The process of claim 18 wherein the acid is selected from the group consisting of aqueous hydrochloric acid and aqueous sulfuric acid.

* * * * *